United States Patent
Rampersad et al.

(10) Patent No.: US 7,568,353 B2
(45) Date of Patent: *Aug. 4, 2009

(54) METHOD OF STORING BIOLOGICAL SAMPLES

(75) Inventors: Bryce Mark Rampersad, Cheektowaga, NY (US); John Henri Royal, Grand Island, NY (US); Barry Alan Minbiole, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 489 days.

This patent is subject to a terminal disclaimer.

(21) Appl. No.: 11/486,925

(22) Filed: Jul. 14, 2006

(65) Prior Publication Data

US 2007/0033952 A1 Feb. 15, 2007

Related U.S. Application Data

(63) Continuation-in-part of application No. 11/037,097, filed on Jan. 19, 2005, now Pat. No. 7,290,396.

(51) Int. Cl.
- F25B 19/00 (2006.01)
- F25B 9/00 (2006.01)
- F17C 5/02 (2006.01)
- F25D 25/00 (2006.01)

(52) U.S. Cl. .............. 62/51.1; 62/6; 62/47.1; 62/62

(58) Field of Classification Search .......... 62/51.1, 62/6, 457.9, 62, 47.1
See application file for complete search history.

(56) References Cited

U.S. PATENT DOCUMENTS

| | | | |
|---|---|---|---|
| 4,300,356 A * | 11/1981 | Notaro et al. | 62/48.1 |
| 4,967,564 A * | 11/1990 | Strasser | 62/47.1 |
| 6,076,372 A | 6/2000 | Acharya et al. | 62/606 |
| 6,128,914 A | 10/2000 | Tamaoki et al. | 62/440 |
| 6,205,794 B1 | 3/2001 | Brothers | 62/51.1 |
| 6,226,997 B1 * | 5/2001 | Vago | 62/130 |
| 6,327,865 B1 | 12/2001 | Bonaquist et al. | 62/79 |
| 6,397,620 B1 | 6/2002 | Kelly et al. | 62/275 |
| 6,426,019 B1 | 7/2002 | Acharya et al. | 252/67 |
| 6,430,938 B1 | 8/2002 | Royal et al. | 62/6 |
| 6,640,552 B1 | 11/2003 | Rampersad et al. | 62/6 |
| 7,076,960 B2 * | 7/2006 | Takemasa | 62/6 |
| 7,290,396 B2 * | 11/2007 | Rampersad et al. | 62/6 |
| 2005/0016198 A1 * | 1/2005 | Wowk et al. | 62/371 |
| 2006/0048522 A1 * | 3/2006 | Yamada | 62/6 |

* cited by examiner

*Primary Examiner*—William C Doerrler
(74) *Attorney, Agent, or Firm*—David M. Rosenblum

(57) ABSTRACT

A method of storing biological samples in which the biological samples are stored in a stack within a vessel interior of an insulated vessel. A pool of liquid cryogen is maintained within the vessel interior by condensing cryogenic vapor boiled off of the pool of liquid cryogen with a cryocooler having a cold finger. The cryocooler and cold finger are positioned so that a cold heat exchanger of the cold finger is in thermal contact with the cryogenic vapor and is positioned above the stack, so as to also maintain a temperature difference within the insulated vessel, between a bottom region of the stack and a top region of the stack, of no greater than about 65K.

6 Claims, 2 Drawing Sheets

METHOD OF STORING BIOLOGICAL SAMPLES

RELATED APPLICATIONS

This application is a continuation-in-part of prior application Ser. No. 11/037,097, filed Jan. 19, 2005 now U.S. Pat. No. 7,290,396.

TECHNICAL FIELD

This invention relates generally to storage and preservation of biological samples and, more particularly, to preservation of biological samples at cryogenic temperatures.

BACKGROUND ART

There is a growing trend toward cryogenic storage of biological samples at temperatures below 140K. This trend is driven by the fact that little to no sample degradation occurs below the sample glass transition temperature which is about 140K. Conventional cryogenic biological sample preservation units that store biological samples at temperatures below 140K use liquid cryogen, such as liquid nitrogen, to keep the biological samples cold. These units typically store the samples within a vacuum insulated space above a pool of liquid cryogen or immersed within the pool of liquid cryogen. The liquid cryogen needs to be periodically replenished. This is costly, not only because of the cost of the cryogen, but also because of the complicated procedures required to handle the liquid cryogen.

SUMMARY OF THE INVENTION

One aspect of the invention is:

A method of storing biological samples in which the biological samples are stored in a stack within a vessel interior of an insulated vessel. The insulated vessel has a lid positioned within an opening allowing the biological samples to be raised from and lowered in to the vessel interior. A pool of liquid cryogen is maintained within the vessel interior by condensing cryogenic vapor boiled from the pool of liquid cryogen with a cryocooler having a cold finger. The cryocooler and cold finger are positioned so that a cold heat exchanger of the cold finger is in thermal contact with the cryogenic vapor and is positioned above the stack so as to also maintain a temperature difference within the insulated vessel, between a bottom region of the stack and a top region of the stack, of no greater than about 65K.

As used herein the term "cryocooler" means a refrigerator which can produce refrigeration below about 140K for the purpose of cooling biological samples.

As used herein the term "cold head" means the portion of the cryocooler containing the cold heat exchanger, aftercooler and regenerator.

As used herein the term "cold finger" means a portion of a cold head that is configured such that the cold heat exchanger is located at one end of the cooled head. The cold finger refers to the portion of the cold head with this configuration that, in operation, is at a temperature below that of the aftercooler.

As used herein the term "biological sample" means an organic material. Some examples of biological samples are proteins, blood platelets, cartilage and heart valves.

DETAILED DESCRIPTION

Figure 1:
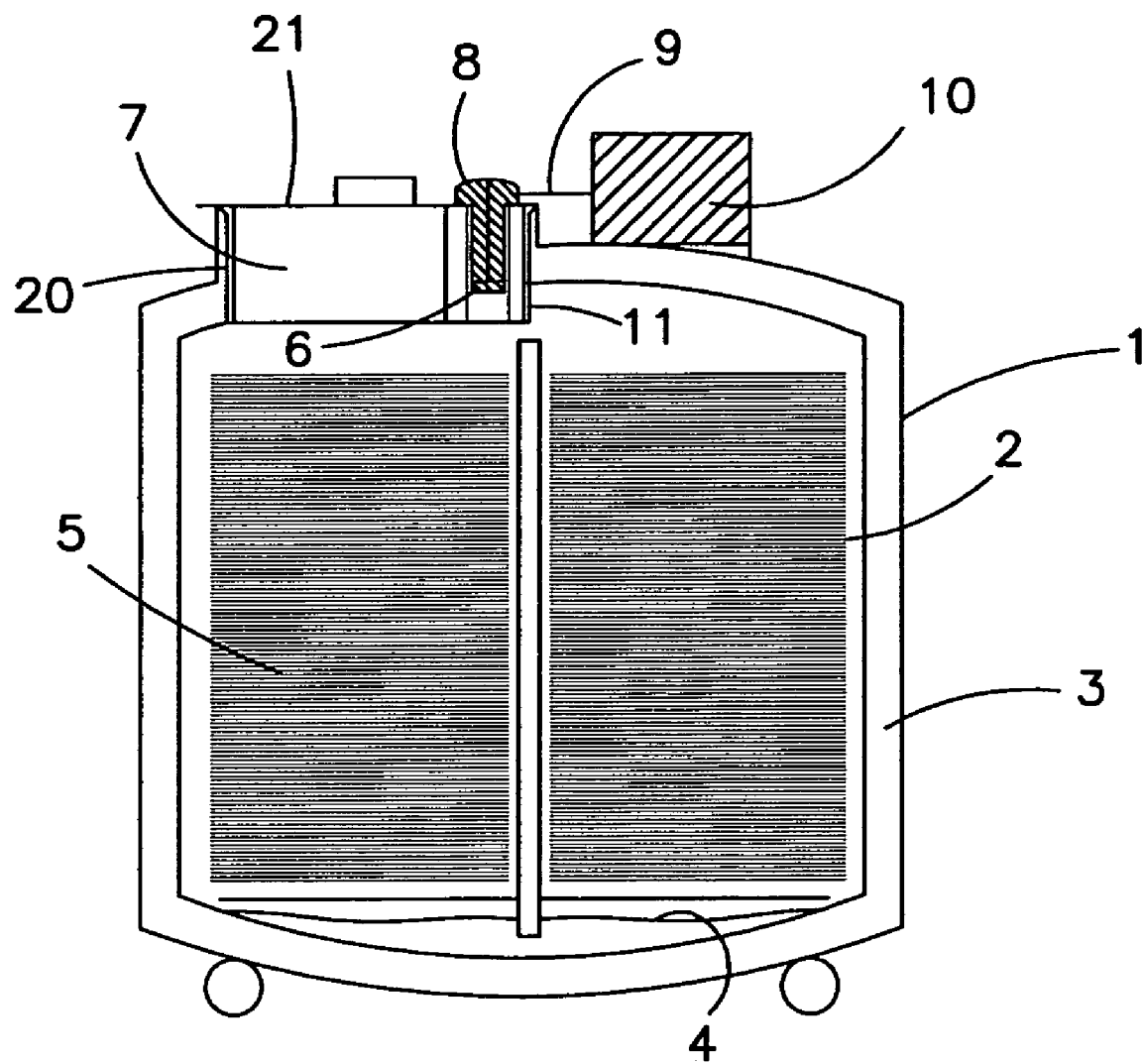
FIG. 1 is a cross sectional representation of one preferred embodiment of the cryogenic biological preservation unit of this invention wherein the lid has a fixed portion and a removable portion and the cryocooler cold finger penetrates at least in part the fixed portion of the lid.

The invention will be described in detail with reference to the Drawings. Referring now to FIG. 1, there is shown a cryogenic biological preservation unit having a vessel wall 1 and having insulation, typically vacuum insulation, 3 adjacent the inside of vessel wall 1. Vessel wall 1 and insulation 3 define the vessel interior or storage space 2. In the lower portion of vessel interior 2 is a pool of liquid cryogen 4. Generally and preferably the liquid cryogen comprises liquid nitrogen. Other liquid cryogens may be used in the practice of the invention provided that they have a normal boiling point below 140K.

Within vessel interior 2 and preferably above liquid cryogen pool 4 there is stored at least one biological sample. In FIG. 1 there is illustrated in representational form a plurality of biological samples in a stack 5, preferably on a known rack system. In general the cryogenic biological preservation unit of this invention will have a diameter within the range of from 30 to 60 inches and a height within the range of from 45 to 75 inches. Depending upon the size of the biological samples and upon the type of rack system used, the cryogenic biological preservation unit of this invention can accommodate or store up to 15,000 to 80,000 biological samples in 1-2 ml plastic vials. Large items such as blood bags and organs can also be stored.

The cryogenic biological preservation unit of this invention has an opening 20 which allows access to the vessel interior 2 from outside the vessel and through which biological samples are put into and removed from the vessel interior. Within opening 20 there is positioned lid 21 which is typically insulated using a closed cell foam such as expanded polystyrene, and which is positioned in opening 20 when access to vessel interior 2 is not desired. In the embodiment of the invention illustrated in FIG. 1, lid 20 comprises a fixed portion 11 and a removable portion 7. The removable portion 7 is removed from opening 20 when access to vessel interior 2 is desired.

Any suitable cryocooler may be used in the practice of this invention. Among such cryocoolers one can name Stirling cryocoolers, Gifford-McMahon cryocoolers and pulse tube refrigerators. A pulse tube refrigerator is a closed refrigeration system that oscillates a working gas in a closed cycle and in so doing transfers a heat load from a cold section to a hot section. The frequency and phasing of the oscillations is determined by the configuration of the system. The driver or pressure wave generator may be a piston or some other mechanical compression device, or an acoustic or thermoacoustic wave generation device, or any other suitable device for providing a pulse or compression wave to a working gas. That is, the pressure wave generator delivers energy to the working gas within the pulse tube causing pressure and velocity oscillations. Helium is the preferred working gas; however any effective working gas may be used in the pulse tube refrigerator and among such one can name nitrogen, oxygen, argon and neon or mixtures containing one or more thereof such as air.

The oscillating working gas is preferably cooled in an aftercooler and then in a regenerator as it moves toward the cold end. The geometry and pulsing configuration of the pulse tube refrigeration system is such that the oscillating working gas in the cold head expands for some fraction of the pulsing cycle and heat is absorbed by the working gas by indirect heat exchange which provides refrigeration to the vessel interior. Preferably the pulse tube refrigeration system employs an inertance tube and reservoir to maintain the gas displacement and pressure pulses in appropriate phases. The size of the reservoir is sufficiently large so that essentially very little pressure oscillation occurs in it during the oscillating flow.

The cryocooler components 10 include the mechanical compression equipment (pressure wave generator), the inertance tube and reservoir, the final heat rejection system and the electrical components required to drive and control the cryocooler. Electrical energy is primarily converted into acoustic energy in the pressure wave generator. This acoustic energy is transferred by the oscillating working gas to the cold head 8 via the transfer tube 9. The transfer tube 9 connects the pressure wave generator to the aftercooler located at the warm end of the cold head 8, where heat is removed as previously described. The cryocooler can be controlled to provide varying amounts of refrigeration to the cold end of the cold finger 6 depending on the conditions in the cryogenic biological preservations unit vessel interior 2. This is accomplished by modulating the acoustic power output from the pressure wave generator by varying the voltage and thus the electrical power supplied. The cryocooler would preferably be controlled based on the temperature of the vessel interior 2 of the cryogenic biological preservation unit.

In the embodiment of the invention illustrated in FIG. 1, cold finger 6 penetrates into vessel interior 2 and provides refrigeration directly to the vessel interior. The refrigeration cools and condenses cryogen vapor within the upper portion of the vessel interior 2 thus significantly reducing the need to replenish the liquid cryogen from outside the unit and thereby minimizing costly and complicated cryogen handling procedures and systems. The condensed cryogen falls by gravity or is directed back to the liquid cryogen pool in the lower portion of the vessel interior.

The temperature at the lowest level of the sample storage within the vessel interior may be as low as 77K and is generally within the range of from 80 to 95K. However, the normal temperature at the upper levels of the sample storage may be within the range of from about 95K to 140K, typically about 120K without the use of the integrated cryocooler of this invention. Samples in the top racks of conventional cryogenic biological preservation units could exceed the glass transition temperature of the biological samples when the lid is removed for access to the interior. For this reason, storage of biological samples in the upper portion of conventional cryogenic biological preservation units is often avoided. However, with the cryogenic biological preservation unit of this invention which provides cryocooler refrigeration to the upper portion of the vessel interior, biological samples may be stored in the upper portion of the vessel interior without fear of degradation due to elevated temperature. This increases the effective capacity of the unit which is another advantage of the cryogenic biological preservation unit of this invention over conventional systems. In this regard, where the cryocooler and the cold finger 6 is positioned so that the cold heat exchanger of the cold finger 6 is in thermal contact with the cryogenic vapor and is positioned above stack 5, sufficient refrigeration can be added to the top of the vessel interior 2 so that a temperature difference of no more than about 65K, preferably 20K is created within the vessel interior 2 between top and bottom regions of stack 5 to minimize prior art temperature stratification that potentially increases degradation of the samples stored within warm upper regions of the vessel. Although in illustrated embodiments, the cold finger 6 extends into the vessel interior 2, it is possible to position the cold finger 6 recessed in the lid. Whether cold finger 6 is recessed or extends past the lid, the cold heat exchanger is in thermal contact with the cryogenic vapor. In accordance with the present invention, where liquid nitrogen is used, the top temperature within the vessel interior at the top region of stack 5 is between about 85K and about 120K, preferably, about 100K and a bottom temperature at bottom region of stack 5 is between about 77K and about 95K. The bottom region of stack 5 can either be located within or above the liquid cryogen pool 4 of liquid nitrogen. When located above the liquid nitrogen, the bottom temperature can be between about 78K and about 95K, as given above, preferably about 80K.

Figure 2:
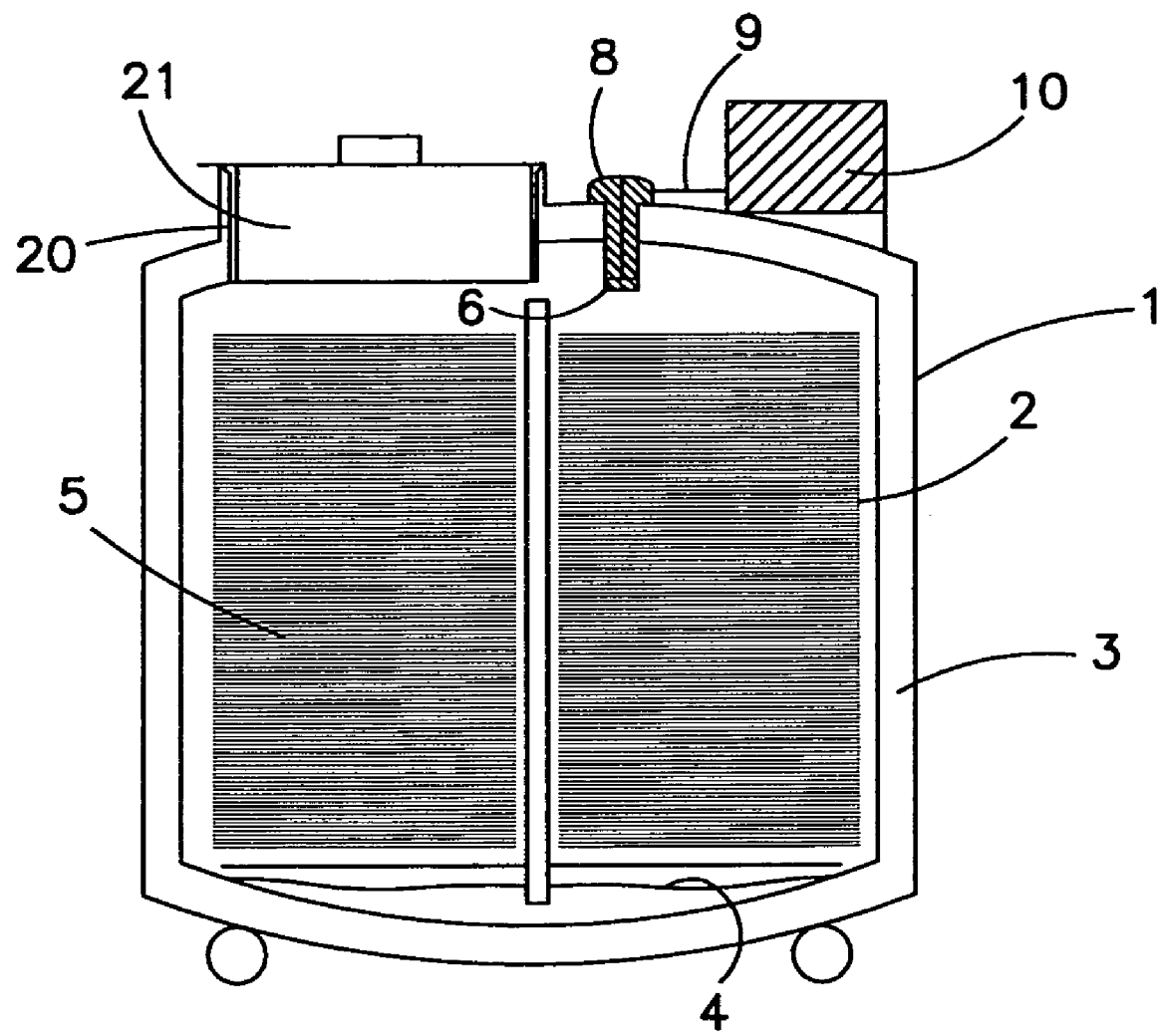
FIG. 2 is a cross sectional representation of another preferred embodiment of the cryogenic biological preservation unit of this invention wherein the cryocooler cold head is positioned apart from the lid.

FIG. 2 illustrates another embodiment of the cryogenic biological preservation unit of this invention. The numerals of FIG. 2 are the same as those of FIG. 1 for the common elements, and these common elements will not be described again in detail. In the embodiment of the invention illustrated in FIG. 2, the lid 21 is comprised entirely of a removable part and the cryocooler cold head 8 is positioned apart from the lid. The cold finger 6 penetrates into the vessel so as to provide refrigeration directly to the vessel interior 2. Alternatively, the cryocooler cold finger could be positioned so that it does not penetrate into the vessel interior but rather provides refrigeration to the inner vessel wall and thus indirectly to the vessel interior. As can be appreciated, the same temperature distribution given above could be provided for the embodiment of FIG. 2.

Although the invention has been described in detail with reference to certain preferred embodiments, those skilled in the art will recognize that there are other embodiments of the invention within the spirit and the scope of the claims.

The invention claimed is:

1. A method of storing biological samples comprising:
storing said biological samples in a stack within a vessel interior of an insulated vessel, the insulated vessel having a lid positioned within an opening allowing the biological samples to be raised from and lowered in to the vessel interior; and
maintaining a pool of liquid cryogen within the vessel interior by condensing cryogenic vapor boiled off from the pool of liquid cryogen with a cryocooler having a cold finger;
the cryocooler and cold finger positioned so that a cold heat exchanger of the cold finger is in thermal contact with the cryogenic vapor and is positioned above the stack so as to also maintain a temperature difference within the insulated vessel, between a bottom region of the stack and a top region of the stack of no greater than about 65K.

2. The method of claim 1, wherein the liquid cryogen is liquid nitrogen, a top temperature is created within the insulated vessel, at the top region of the stack of between about 85K and about 120K and a bottom temperature is created within the insulated vessel, at the bottom region of the stack of between about 77K and about 95K.

3. The method of claim 2, wherein the bottom region of the stack is positioned above the liquid nitrogen, the bottom temperature is about 80K and the top temperature is about 100K.

4. The method of claim 1 or claim 2 or claim 3, wherein the cryocooler is a pulse tube refrigerator.

5. The method of claim 4, wherein the cold finger is positioned within the vessel interior by penetrating, at least in part, a fixed portion of the lid, the lid also having a movable portion to allow access to the vessel interior.

6. The method of claim 4, wherein the cold finger is positioned within the vessel interior by positioning the cold head separate and apart from the lid and with the cold finger penetrating a vessel wall defining the vessel interior.

* * * * *